United States Patent [19]

Dasgupta

[11] Patent Number: 5,138,044
[45] Date of Patent: Aug. 11, 1992

[54] SYNTHESIS OF SIALOSIDES

[75] Inventor: Falguni Dasgupta, Alameda, Calif.

[73] Assignee: Glycomed, Inc., Alameda, Calif.

[21] Appl. No.: 566,682

[22] Filed: Aug. 13, 1990

[51] Int. Cl.$^5$ .......................... C07G 3/00; C07H 5/04; C07H 5/10

[52] U.S. Cl. ................................. 536/18.5; 536/17.5; 536/54; 536/55.2; 536/55.3; 536/4.1; 536/17.1

[58] Field of Search ................ 536/18.5, 17.5, 17.6, 536/54, 122, 118, 119, 120, 55.2, 55.3, 18.7

[56] References Cited

U.S. PATENT DOCUMENTS

| | | | |
|---|---|---|---|
| 4,691,012 | 9/1987 | Ogura et al. | 536/23 |
| 4,694,076 | 9/1987 | Ogawa et al. | 536/17.2 |
| 4,914,035 | 4/1990 | Hasegawa et al. | 536/122 |
| 4,935,506 | 6/1990 | Goto et al. | 536/122 |

FOREIGN PATENT DOCUMENTS

| | | | |
|---|---|---|---|
| 346814 | 12/1989 | European Pat. Off. | 536/54 |
| 61-282390 | 12/1986 | Japan | 536/17.5 |
| 63-41494 | 2/1988 | Japan | 536/17.5 |
| 64-52794 | 2/1989 | Japan | 536/17.5 |

*Primary Examiner*—Johnnie R. Brown
*Assistant Examiner*—Everett White
*Attorney, Agent, or Firm*—Morrison & Foerster

[57] ABSTRACT

Reaction schemes for carrying out a variety of chemical synthesis are disclosed. The reactions produce α-(X)-sialosides wherein X is O, S, N or another compatible electron donating atom or molecular moiety. The reaction schemes include a relatively small number of steps to provide a yield with a relatively small amount of undesired β-configuration product. Compounds synthesized are encompassed by the following general structural formula I.

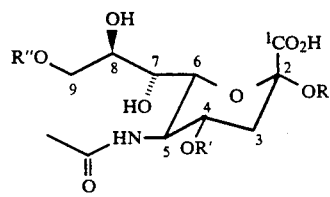

wherein R, R' and R" are each independently H, $CH_3$, acetyl, or a disaccharide which is preferably lactose.

2 Claims, 3 Drawing Sheets

SYNTHESIS OF SIALOSIDES

FIELD OF THE INVENTION

This invention relates generally to the field of chemical synthesis. More specifically this invention relates to efficient, abbreviated synthesis schemes for producing compounds which are sialic acid derivatives.

BACKGROUND OF THE INVENTION

Sialic acids represent a number of complex higher saccharides, most of which are terminally bound to glycoproteins and glycolipids of various tissues of animals. Sialic acids which are α-linked to glycolipids and glycoproteins that occur on cell surface, have a major role in cellular recognition processes. (See R. Schauer, *Adv. Carbohydr. Chem. Biochem.* (1982) 40:131-134, and R. Schauer, *Cell Biology Monographs,* Vol. 10 (1982) Springer-Verlag, N.Y., Wien.)

In the case of infection by influenza virus, the specific interaction between the hemagglutinin (HA, one of the major glycoproteins on the surface of the virus) with sialic acid in its α-conformer is the only known phenomenon by which the attachment of the virus to the host cell occurs, prior to its entry and proliferation within the cell. (See D. C. Wiley et al., *Ann. Biochem.* (1987) 56:365-394, and D. C. Wiley in *Virology.* B. N. Fields, ed., (1985) pp. 45-68, New York.) The receptor site on HA is the extracellular globular domain. (See I. A. Wilson et al., *Nature* (1981) 289:366-373, and D. C. Wiley et al., *Nature* (1981) 289:373-378.) It is trimeric, consisting of three conserved pockets of amino acids. Therefore, in every case of infection the receptor on the virus is this globular domain whose binding to the host cell is mediated through α-sialic acid on the cell surface. The exact interaction that occurs, involving various amino acids in the pocket with the functionalities on the sialic acid has been determined by X-ray crystallographic studies as shown in FIGS. 1 and 2 and described in W. Weis et al., *Nature* (1982) 333:131-234.

There are thirteen antigenically distinct HAs that have been demonstrated in human, swine, avian and equine isolates (see Hinshaw et al. in *Basic and Applied Research* (A. S. Bear, ed.) 1982, vol. 2, pp. 1082-96, Elsovier, Amsterdam). Thus, whereas some strains are SAα(2,3)Gal specific, the other would recognize SAα(2,6)Gal on the cell surface. In addition, some HAs would recognize 4-O-acetyl-N-acetyl neuraminic acid, a sialic acid characteristic of the equine species (H. P. Schauer et al., *Biochem. Soc. Symp.* (1974) 131:394–400). These exhibited variations have been shown to be species specific. Influenza strains that infect human cells recognize SAα(2,6)Gal.

A major outcome of these studies is the observation that sialic acid residues are recognized only in their α-anomeric configurations. Whereas the α-anomer is more abundant in nature, chemical reactions with sialic acid has shown that in solution, during glycosidation, the β-anomer forms preponderantly, indicating it to be the thermodynamically preferred structure. Synthesis of oligosaccharides containing α-sialosides as the terminal (non-reducing end) moiety have been a challenge to carbohydrate chemists. Attempts to prepare such molecules generally involved methods commonly utilized for glycosidation reactions. Synthesis of α-sialosides have been done using methyl 5-acetamido-4,7,8,9-tetra-O-acetyl-2-chloro-3,5-di-deoxy-D-glycero-D-galacto-2-nonulopyranosonate (which compound is shown in Reaction Scheme 2 below as compound 1) as the donor under Knoenigs Knor conditions (see Koenig et al., *Chem. Ber.* (1901) 34:957) or modification thereof using silver or mercury salts (R. Schauer et al. (eds.), "Proceedings of the Japanese-German Symposium on Sialic Acid" May 18-21, 1988; T. Ogawa et al., *Carbohydr. Res.* (1985) 135 C5-C9; H. Ijima et al., *Carbohydr. Res.* (1989) 186:107-118; V. Pozsgay et al., *J. Carbohydr. Chem.* (1987) 6:41-55; D. J. M. van der Vleugel et al., *Carbohydr. Res.* (1982) 102:121-130; N. Bagett et al., *Carbohydr. Res.* (1982) 110:11-18). The resulting products have been found to be largely contaminated with the β-linked isomer.

Thioglycosides as the glycosyl donors have been extensively used in oligosaccharide synthesis. Their increasing importance for glycosylation reaction is mainly due to a number of thiophilic activators that have been introduced for direct synthesis of α- and β-glycosides from the corresponding thioglycosides. (See F. Dasgupta et al., *Carbohydr. Res..* UK 4089 (1990) 202, 229-238; F. Dasqupta et al., *Carbohydr. Res:* (1988) 177, C13-C17; P. Fugedi et al., *Carbohydr. Res.* (1986) C6-C10; P. Fugedi et al., *Glycoconjugate J.* (1987) 4:97-108; Y. Ito et al., *Tetrahedron Lett.* (1988) 29:1061-1069; Y. Ito et al., *Tetrahedron Lett.* (1988) 29:4701-4706; V. Pozsgay et al., *J. Org. Chem.* (1987) 52:4635-4637; and H. Lonn, *Carbohydr. Res.* (1985) 139:105-113, 115-121.

For the preparation of α-sialosides, most consistent results have been obtained using methyl 5-acetamido-4,7,8,9-tetra-O-acetyl-3,5-di-deoxy-2-methyl-2-thio-D-glycero-α-D-galacto-2-nonulopyranosonate in conjunction with dimethyl (methylthio) sulfonium trifluoromethane sulfonate (DMTST) as the thiophilic promoter (Fugedi et al. *Carbohydr. Res.* (1986) C6-C10). This method of coupling has been extensively used by Kiso and Hasegawa and has proved to be of value for the synthesis of α-sialoside containing oligosaccharides. (See A Hasegawa et al., *J. Carbohydr. Chem.* (1986) 5:11-19.)

However, synthesis of this α-thiosialoside required a number of steps starting from compound 1 (shown in FIG. 3) and also used the carcinogenic reagent, methyl iodide (A. Hasegawa et al., *J. Carbohydr. Chem.* (1986) 5:11-19; O. Kanie et al., *J. Carbohydr. Chem.* (1988) 7:501-506). In addition, the method could not be of general use, e.g., it is not possible to make by this method α-phenyl thiosialoside, an equally effective and sometimes a thioglycoside of choice during sialosidation reaction.

The most prominent sialic acid is N-acetylneuramic acid, which occurs mainly α, 2→3 or α, 2→6-glycosyldically linked to the preterminal sugars. Specific synthesis methods for producing N-acetylneuraminic acid and the glycal derivatives is described by E. Kerchner et al., *J. Carbohydr. Chem.* (1988) 10(2), 453-486, which is incorporated herein by reference. This publication specifically teaches the use of potassium methoxide as a catalyst to promote the formation of the α- as opposed to the β-thioglycoside.

The present invention endeavors to solve the synthesis problems of the prior art by reducing the reaction steps needed and/or improving the yield of the α-configuration obtained.

SUMMARY OF THE INVENTION

The present invention provides a general method for the preparation of α-2-S-glycosides of sialic acid. Application of the same technique can be extended to prepare α-2-O-sialosides. It will also be shown that the technique can prove useful for the preparation of polysialoside containing supports. These will be useful in the preparation of α-(O,S)-linked sialic acids that will be used in designing of drugs as inhibitors for (a) influenza virus infection and (b) post-infective proliferation of the virus.

A primary object of the present invention is to disclose and describe an efficient chemical synthesis of various α-(X)-sialosides wherein X is O, S, N or another compatible atom or molecular moiety.

An advantage of the present invention is that it can be carried out using a relatively small number of steps.

A feature of the present invention is that it provides a relatively high yield of the desired product with a no or a small amount (none detected) of undesired β-configuration product.

These and other objects, advantages and features of the present invention will become apparent to those persons skilled in the art upon reading the details of the structure synthesis and usage as more fully set forth below, reference being made to the accompanying general structural formulas forming a part hereof wherein like symbols refer to like molecular moieties throughout.

BRIEF DESCRIPTION OF THE DRAWINGS

This invention may be better understood and its numerous objects, advantages and features rendered more apparent to those skilled in the art by reference to the accompanying figures as follows.

DETAILED DESCRIPTION OF PREFERRED EMBODIMENTS

Figure 1:
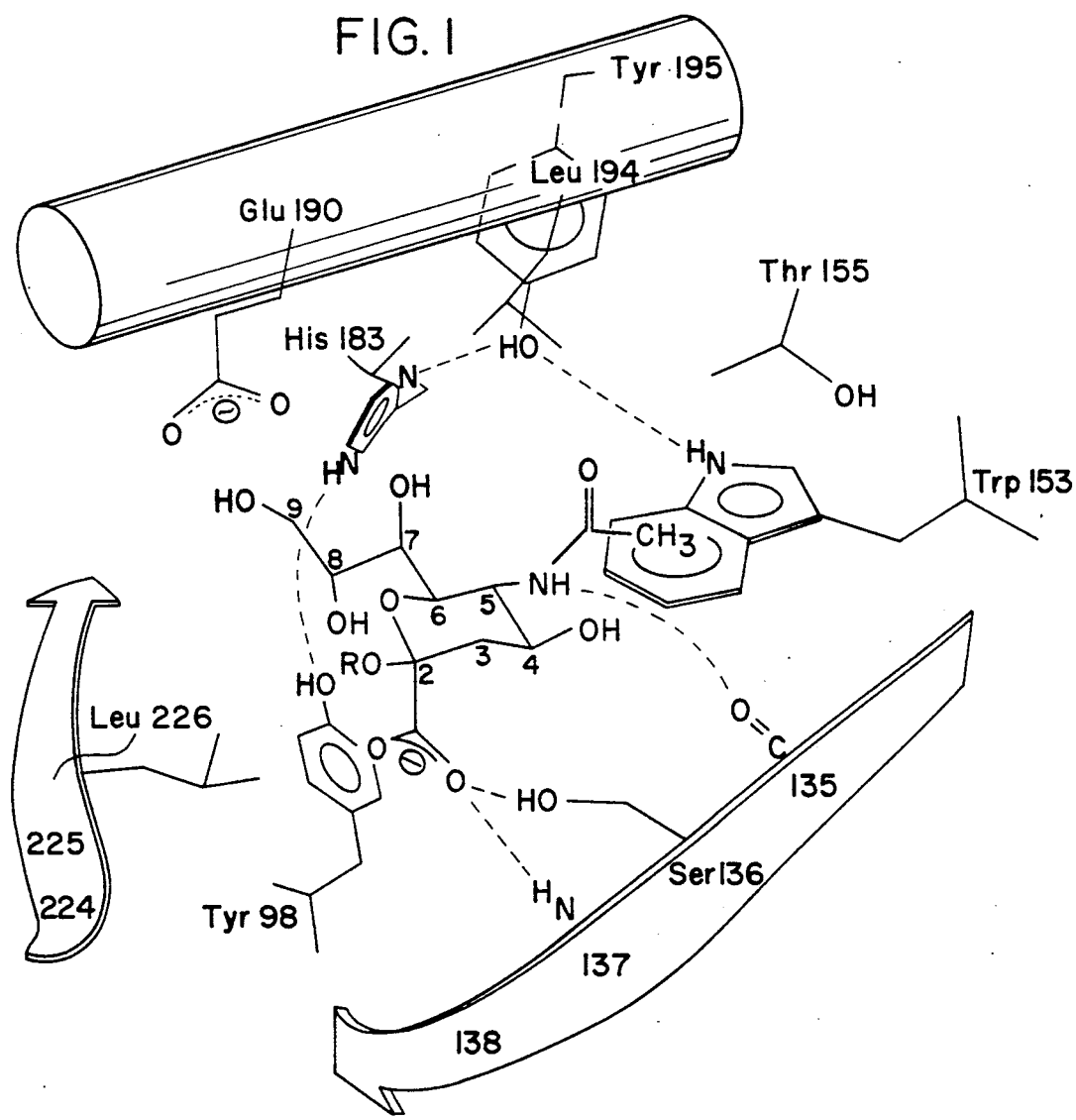
FIG. 1 is a schematic diagram of sialic acid bound to X-31 hemagglutinin based on the crystal structure determined at a resolution of 3 Å as shown in W. Weir et al., Nature (1988) 333, 426–431.
Figure 2:
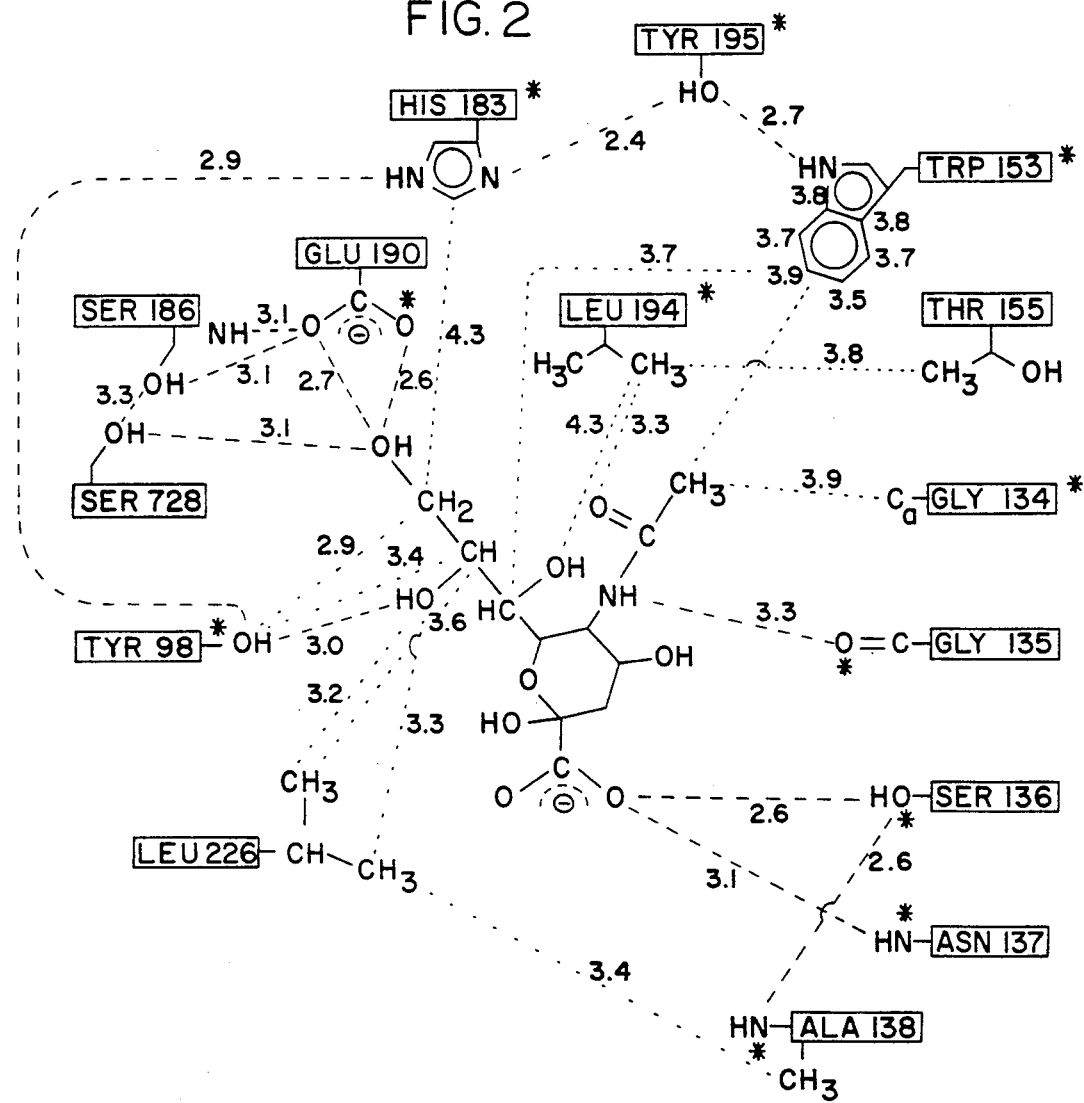
FIG. 2 is a schematic diagram of sialic acid showing interactions with various amino acids.
Figure 3:
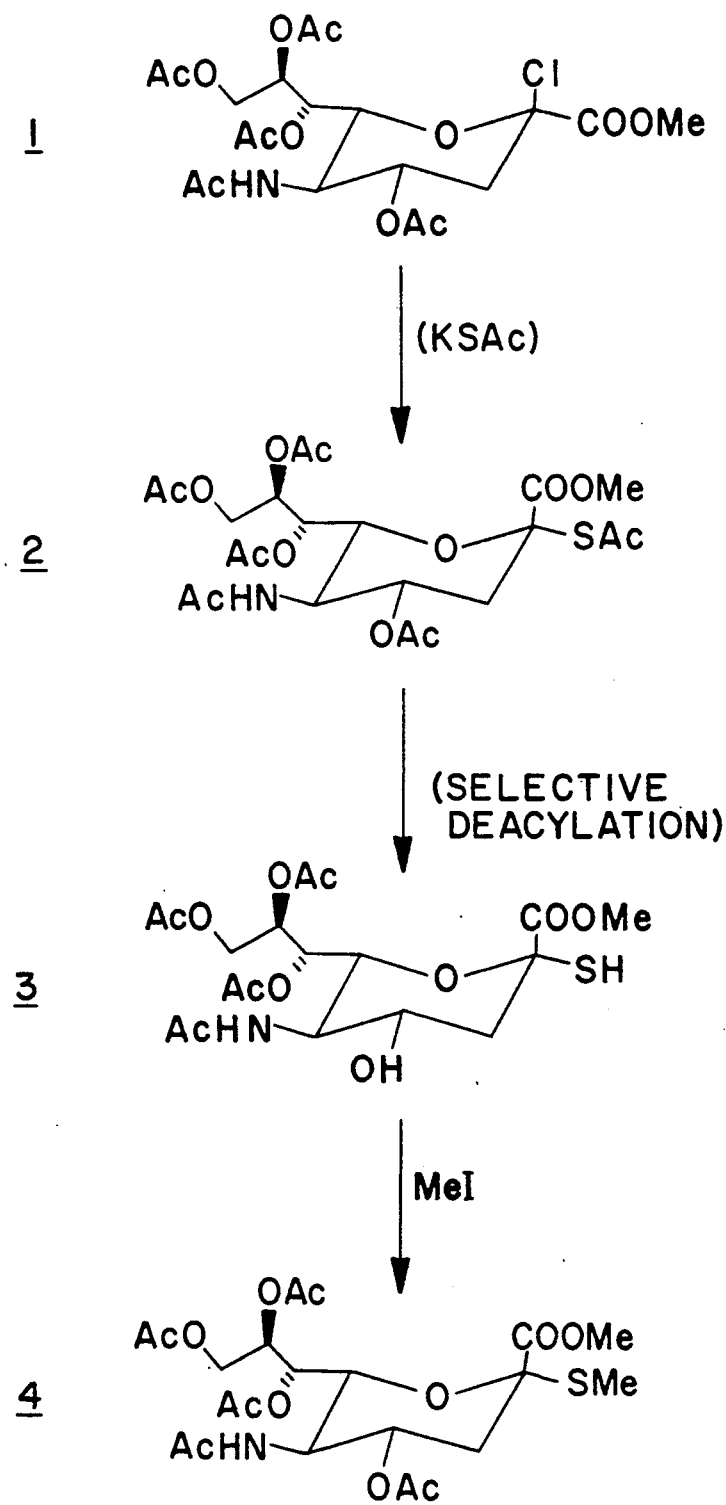
FIG. 3 is a reaction scheme showing a synthesis of α-thiosialoside.

Before the synthesis methods of the present invention are described, it is to be understood that this invention is not limited to the particular steps or processes described as such methods may, of course, vary. It is also to be understood that the terminology used herein is for the purpose of describing particular embodiments only, and is not intended to be limiting since the scope of the present invention will be limited only by the appended claims.

It must be noted that as used in this specification and the appended claims, the singular forms "a", "an" and "the" include plural referents unless the context clearly dictates otherwise. Thus, for example, reference to "a sialoside" includes mixtures of sialosides, reference to "an acid" includes reference to mixtures of such acids, reference to "a step" includes various combinations of such steps of the type described herein and of the type that will become apparent to those persons skilled in the art upon reading this disclosure and so forth.

The synthesis methods of the present invention result in the production of various forms of α-linked sialic acids encompassed by the following general structural formula I:

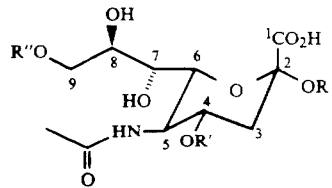

wherein R, R' and R" are each independently H, $CH_3$, acetyl, or a disaccharide which is preferably lactose.

In some preferred embodiments of the present invention the variables of R, R' and R" are defined as follows:

1) R is H, R' is H and R" is H which is N-acetylneuraminic acid (Neu 5Ac);
2) R is —$CH_3$, R' is H and R" is H which is NEU5Acα2Me, the symbol Ac is acetyl throughout and Me is —$CH_3$ throughout;
3) R is lactose, R' is H and R" is H which is sialyllactose;
3a) R is (2,3)Galβ(1,4)Glc, R' and R" are each H which is α-(2,3)sialyllactose;
3b) R is (2,6)Galβ(1,4)Glc, R' and R" are each H which is α(2,6) sialyllactose;
4) R is H, R' is Ac, R" is H which is Neu4,5Ac$_2$;
5) R is H, R' is H and R" is Ac which is Nue5,9Ac$_2$.

The following Reactions Schemes 1–7 are included so as to provide those of ordinary skill in the art with a complete disclosure and description of how to carry out the methods of synthesis of the invention; they are not intended to limit the scope of what the inventors regard as their invention. Efforts have been made to insure accuracy with respect to numbers used (e.g., times, temperature, etc.) but some experimental errors and deviation should be accounted for. Unless indicated otherwise, conventional protocol methodology used by those skilled in the art are used, temperature is in degrees C., and pressure is at or near atmospheric.

Throughout this disclosure, conventional abbreviations are used, e.g., Me is methyl; Et is ethyl, Ph is phenyl; Ac is acetyl, and R.T. is room temperature.

Reaction Scheme 1

Generalized Method

The following is a generic method for the preparation of α-(X)-sialosides wherein X is N, O, S or another compatible nucleophilic atom or moiety.

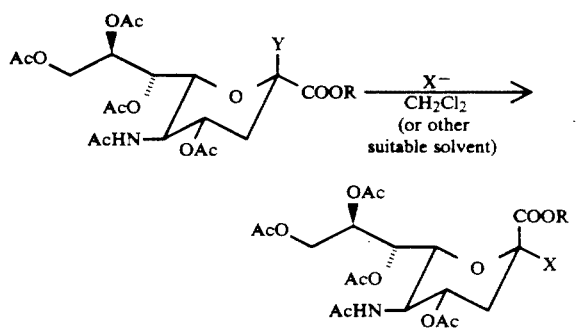

wherein Y is a leaving group such as a halogen or a sulfonate ester, and R is an alkyl moiety which may be a simple hydrocarbon (preferably methyl) or a hydrocarbyl which will include heteroatoms or groups having an electron-withdrawing characteristic or contribute to steric hindrance.

By carrying out the synthesis of Reaction Scheme 1, different "X"-contributing reactants can be used so that the "X" can be varied and a number of products may be produced. The following four structures show variations of the right half of the above reaction product. The by-products may also have useful applications similar to the main reaction product shown on the far right.

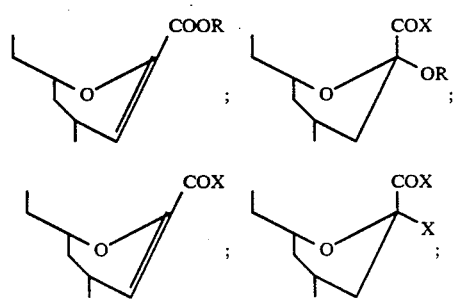

Reaction Scheme 2

Synthesis of methyl 5-acetamido-4,7,8,9-tetra-O-acetyl-3,5-di-deoxy-2-phenyl-2-thio-D-glycero-α-D-galactononulopyranosonate.

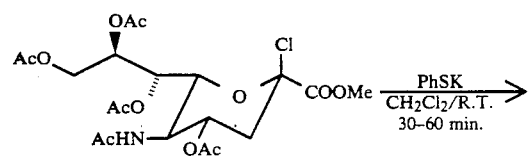

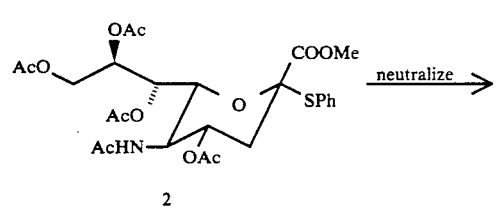

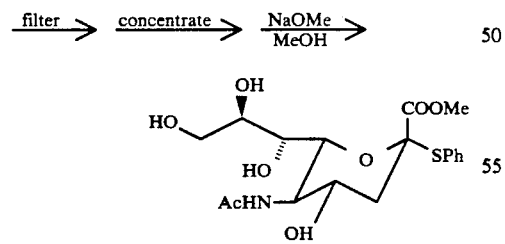

Yield (1→3) ~60–65%. m.p. 205°–206° C. $[\alpha]^{20}_D = +78°$ C. $[\alpha]^{20}_{436} = +163°$ C. (c 1.31, MeOH).

Elem. Anal. Calc. for $C_{18}H_{25}NO_8S$: C, $S_2O_4$; H, 6.07; N, 3.37. Found: C, 52.01; H, 6.1; N, 3.38.

Reaction Scheme 3

Synthesis of methyl 5-acetamido-4,7,8,9-tetra-O-acetyl-3,5-di-deoxy-2-ethyl-2-thio-D-glycero-α-D-galacto-2-nonulopyranosonate.

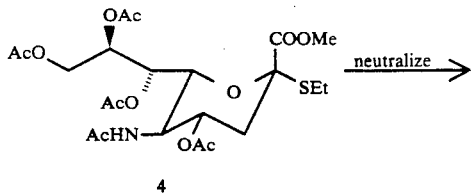

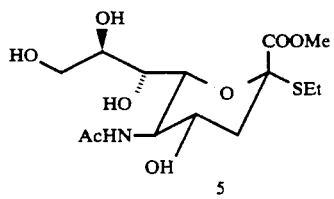

Yield (1→5) ~60%. m.p. 158°–159° C. $[\alpha]^{20}_D = +52.5°$ C. $[\alpha]^{20}_{436} = +119.3°$ C. (c0.8, MeOH).

Elem. Anal. Calc. for $C_{14}H_{25}NO_8S$: C, 45.7; H 6.86; N, 3.81. Found: C, 45.96; H, 7.16 and N, 3.63.

Reaction Scheme 4

Reaction of methyl 5-acetamido-4,7,8,9-tetraacetyl-2-chloro-3,5-di-deoxy-D-glycero-D-galacto-2-nonulopyranosonate(1) with potassium allyloxide.

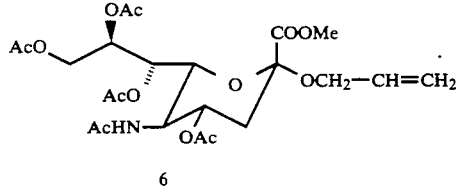

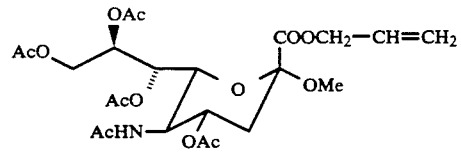

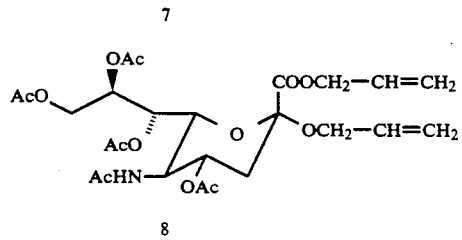

Reaction Scheme 5

Reaction of methyl-5-acetamido-4,7,8,9-tetraacetyl-2-chloro-3,5-di-deoxy-D-glycero-D-galacto-2- nonulopyranosonate (1) with KOCH3 in suitable solvent such as CH2Cl2.

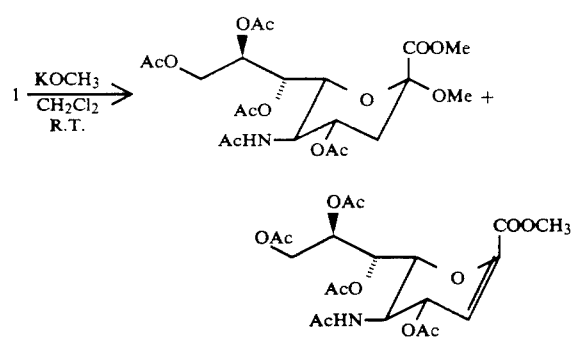

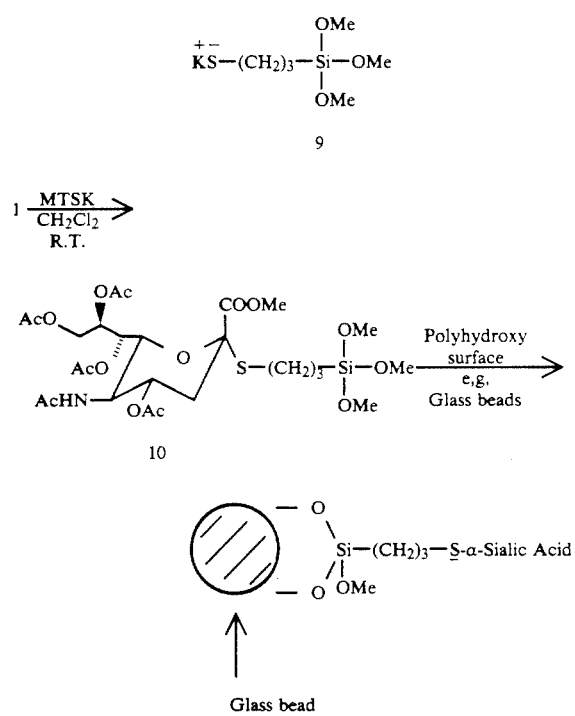

Reaction Scheme 6

Synthesis of sialic acid derivative for attachment to polyhydroxylic surfaces/supports. Reagent:

In the above MTSK is 3-mercaptopropyltrimethoxy silyl potassium.

Reaction Scheme 7

In an alternative approach, the polyhydroxy support base surface can be pretreated with 3-mercaptopropyl trimethoxy silane and then reacted with the compound 1 above under strongly basic conditions. This reaction scheme is shown below:

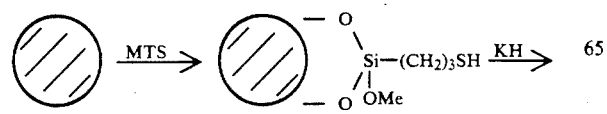

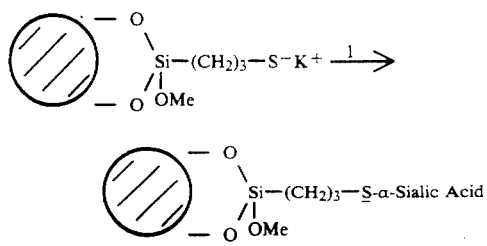

In the instant invention is shown and described herein in what is considered to be the most practical, and the preferred embodiments. It is recognized, however, that departures may be made therefrom which are within the scope of the invention, and that obvious modifications will occur to one skilled in the art upon reading this disclosure.

What is claimed is:

1. A method of synthesis, comprising the steps of:
reacting a compound of formula 1 with a compound of formula 9 to obtain a compound of formula 10 as follows:

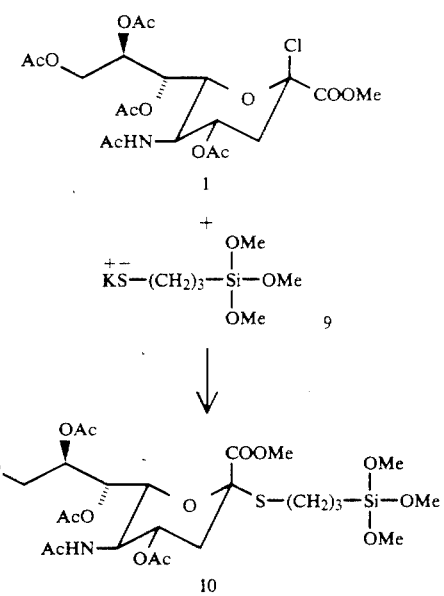

wherein the reaction of the compound of formula 1 and the compound of formula 9 is carried out in a suitable solvent and at a temperature sufficient to allow the reaction to proceed to obtain the compound of formula 10;

reacting the compound of formula 10 with a substrate surface having polyhydroxyl groups thereon, wherein the substrate is glass beads and the reaction provides a product as follows:

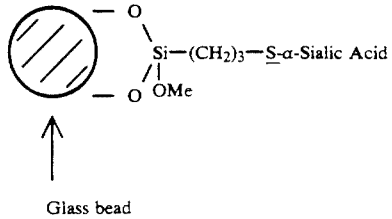

2. A method of synthesis, comprising the steps of:
   treating a substrate surface having polyhydroxyl groups thereon with a compound of formula 9

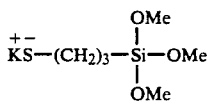

to thereby provide a treated substrate surface with the compound of formula 9 therein; and
   reacting a compound of formula 1 with the treated substrate surface

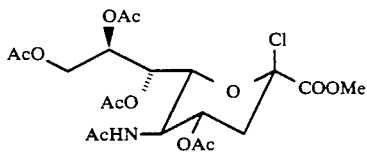

wherein the reaction of the compound of formula 1 with the treated substrate surface is carried out in a suitable solvent, under strongly basic conditions at a temperature sufficient to allow the reaction to proceed.

* * * * *